US00PP12848P2

(12) United States Plant Patent
de Jong

(10) Patent No.: US PP12,848 P2
(45) Date of Patent: Aug. 13, 2002

(54) BOUVARDIA PLANT NAMED 'ROYAL JANETTE'

(76) Inventor: John M. F. de Jong, Floraweg 67-2371 Am, Roelofarendsveen (NL)

( * ) Notice: Subject to any disclaimer, the term of this patent is extended or adjusted under 35 U.S.C. 154(b) by 0 days.

(21) Appl. No.: 09/414,163

(22) Filed: Oct. 8, 1999

(51) Int. Cl.[7] ..... A01H 5/00
(52) U.S. Cl. ..... Plt./352
(58) Field of Search ..... Plt./352

(56) References Cited

U.S. PATENT DOCUMENTS

PP6,723 P * 4/1989 De Jong ..... Plt./352
PP7,867 P * 5/1992 De Jong ..... Plt./352

OTHER PUBLICATIONS

Huxley, A. ed. The New Royal Horticultural Society Dictionary of Gardening, The Stockton Press, New York: Jul. 1992, vol. 1 pp. xxiv–xxvi, 379, 380.*

UPOV–ROM GTITM Computer Database, GTI JOUVE Retrieval Software, citations for 'Royal Janette', Aug. 2000.*

European Union Community Plant Variety Office Decision No. 7010.

European Union Certificate on the Grant of Community Plant Variety Rights No. 7010; Nov. 20, 2000.

Plant Varieties Journal No. 37, Canadian Applications Under Examination; Oct., 2000, Canada.

Plant Breeder's Rights Office, application (published Apr. 16, 1998), denomination (published Mar. 6, 1998), decision (published Sep. 16, 1998); The Netherlands.

* cited by examiner

*Primary Examiner*—Bruce R. Campell
*Assistant Examiner*—Anne Marie Grunberg
(74) *Attorney, Agent, or Firm*—Foley & Lardner

(57) ABSTRACT

A new and distinct cultivar of Bouvardia plant named 'Royal Janette' characterized by having bright orange/red flowers, dark-green foliage, short internodes, which makes it suitable for growing as a potplant, and excellent keeping quality.

1 Drawing Sheet

BACKGROUND OF THE INVENTION

The present invention comprises a new and distinct cultivar of Bouvardia plant, botanically known as Bouvardia Salisb., and hereinafter referred to by the cultivar name 'Royal Janette'. Bouvardia is native to Mexico and other countries of Central America. The genus is named after the French medical doctor Charles Bouvard who lived from 1572 to 1657.

The genus Bouvardia is a member of the family Rubiaceae and mainly contains small shrubs. Generally, the flowers of Bouvardia contain a four-lobed calyx and a long tubular, funnel-shaped, corolla with four spreading lobes. There are two carpels and two stigmas and the fruit is a capsule.

Bouvardia plants are generally propagated by soft tip cuttings. For example, plants of the new variety are pruned under temperature conditions which prevent flower bud formation (20–22° C.). Young shoots with at least two well-developed leaf pairs are rooted.

'Royal Janette' is a product of a planned breeding program which had the objective of creating new Bouvardia cultivars having improved quality and flowers of various colors. 'Royal Janette' was originated from a crossing made by the inventor in a controlled breeding program in Roelofarendsveen, the Netherlands, in 1990. The female parent was a proprietary Bouvardia selection designated 94.423.18. The male parent was a proprietary Bouvardia selection designated 94.423.7. 'Royal Janette' was discovered and selected as one flowering plant within the progeny of the stated cross by the inventor, John M. F. de Jong, in a controlled environment in Roelofarendsveen, the Netherlands.

The first act of asexual reproduction of 'Royal Janette' was accomplished when soft tip cuttings were taken from the initial selection in October 1997 in a controlled environment in Roelofarendsveen, the Netherlands by John M. F. de Jong. Horticultural examination of selected units has demonstrated that the combination of characteristics as herein disclosed for 'Royal Janette' are firmly fixed and are retained through successive generations of asexual reproduction.

BRIEF DESCRIPTION OF THE INVENTION

The following traits have been repeatedly observed and are determined to be basic characteristics of 'Royal Janette' which, in combination, distinguish this Bouvardia as a new and distinct cultivar:

1. Bright orange/red flowers;

2. Dark-green foliage;

3. Short internodes, which makes it suitable for growing as a potplant; and

4. Excellent keeping quality.

'Royal Janette' has not been observed under all possible environmental conditions. The phenotype of the new cultivar may vary significantly with variations in environment such as temperature, light intensity, and daylength without any change in genotype. The following observations, measurements, and values describe the new cultivar as grown in Roelofarendsveen, the Netherlands under conditions which approximate those generally used in commercial practice.

BRIEF DESCRIPTION OF THE DRAWING

The accompanying color photographic drawing shows typical flower and foliage characteristics of 'Royal Janette', with colors being as true as possible with illustrations of this type. The photograph shows a top view of the claimed cultivar in bloom showing the flower form.

DETAILED BOTANICAL DESCRIPTION

The following observations, measurements and values describe 2 year old plants of Bouvardia 'Royal Janette' as grown in a green house in the Netherlands, with day temperatures approximately 25° C. and night temperatures approximately 18° C. 4 weeks is required to get the plants to flower a short day (10 hours of light per day).

In the following description, color references are made to The Royal Horticultural Society Colour Chart (R.H.S).

Origin: Seedling from breeding program.

Parentage:

*Male parent.*—Unnamed seedling designated 94.423.7.

*Female parent.*—Unnamed seedling designated 94.423.18.

Classification:

*Botanical.*—*Bouvardia salisb.*

*Commercial.*—Bouvardia cv. Royal Janette.

Plant

*Form.*—A vigorously growing small shrub with oppositely arranged leaves and flowers in terminal cymes.

*Height.*—Up to 80.0 cm.

*Diameter.*—20 cm (2 year old plant, plants for the production of cut flowers).

*Growth habit.*—Vigorous, after pruning the plant takes 12 weeks to produce flowering stems up to 80 cm (plants for the production of cut flowers).

*Hardiness.*—The plant cannot survive temperatures below 0° C.

*Root stock.*—Adventive root system.

*Foliage.*—Quantity: Numerous, 10–15 leaves per stem. Size of leaf: Approximately 5.5–7.0 cm. Shape of leaf: Lanceolate. Apex: Pointed. Base: Narrowed to the petiole. Texture: Smooth. Color: Upper surface is green, RHS 137A; lower surface is green, RHS 138B. Pubescence: Some pubescence displayed. Petiole color: RHS 143C.

Bud:

*Form.*—Flask-shaped.

*Size.*—Small, approximately 0.5 cm in diameter and 1.5–2.0 cm in length.

*Color.*—RHS 39B.

*Pubescence.*—None.

*Peduncle.*—Length: Approximately 4.0–5.0 cm. Texture: Smooth. Form: Erect.

Flower:

*Blooming habit.*—Continuously year-round.

*Size.*—Diameter: 0.5–1.0 cm. Depth: 1.5–2.0 cm.

*Borne.*—Terminal cymes.

*Shape.*—Lobed, tubular corolla.

*Sepals.*—Quantity: 4. Shape: Lanceolate. Size: 0.6 cm long, 0.4 cm wide. Color: RHS 137B.

*Petalage.*—Number of Petals: Four. Arrangement: Concentric circle. Form: Elliptical. Texture: Smooth. Appearance: Satiny. Color: Orange-red, RHS 40B. Outer petals: RHS 45D. Inner petals: RHS 40B to RHS 41B. Persistence: Flowers remain on plant eventually becoming dry. Main stem or stalk: Length: Up to 80.0 cm. Diameter: 0.3 cm. Color: Green, RHS 138B (when not pigmented); RHS 177A when pigmented. Character: Sturdy and erect. Lasting quality of bloom: 14–20 days as a cut flower; 35 days as a pot plant.

Reproductive organs:

*Stamens.*—Number: Four. Arrangement: Alternate with corolla lobes.

*Anthers.*—Size: Approximately 0.25 cm. Color: RHS 1C.

*Filaments.*—Length: Approximately 1.5 cm. Color: White, RHS 155D. Pollen: Dark brown, RHS 200A.

*Pistil.*—Number: One. Color: RHS 155A.

*Fruit.*—Shape: Loculicidal capsule, seeds winged. Size: Length 0.5 cm, width 0.5 cm. Color: 161A.

*Seed.*—Shape: Round. Size: Length 0.19 cm, width 0.18 cm. Quantity: 18 seeds per capsule. Color: Black, RHS 202A.

I claim:

1. A new and distinct cultivar of Bouvardia plant named 'Royal Janette', as illustrated and described herein.

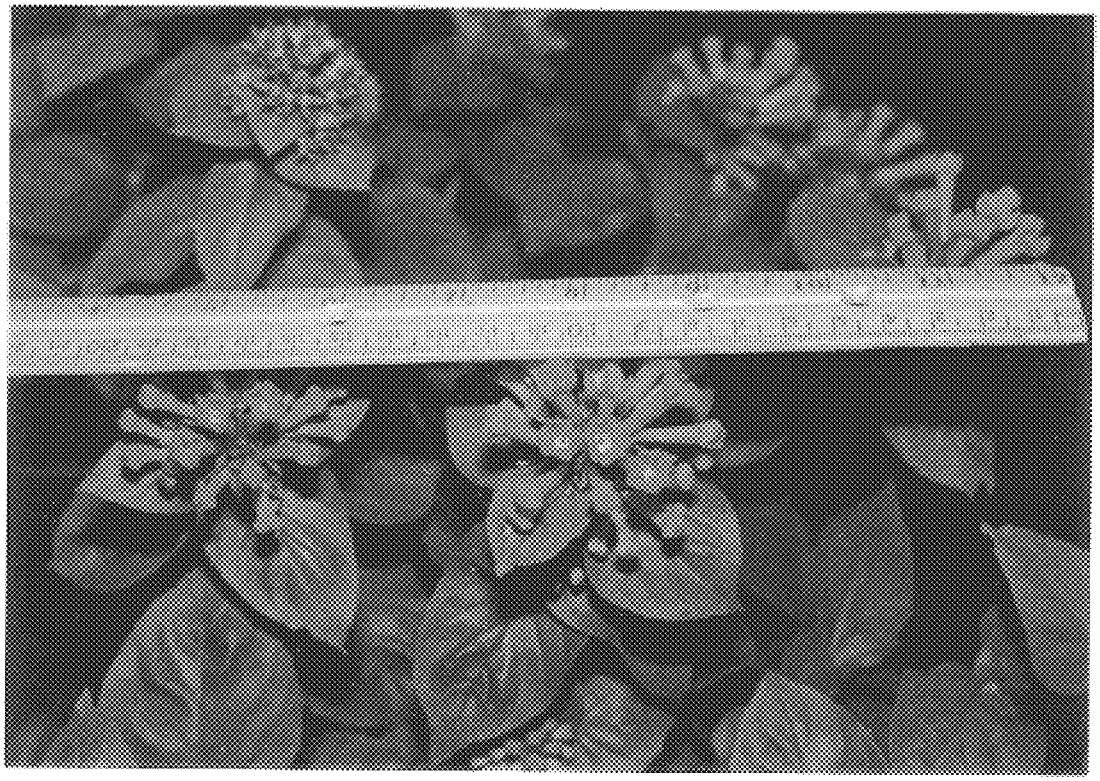

* * * * *